United States Patent [19]

Bürger

[11] Patent Number: 4,983,829
[45] Date of Patent: Jan. 8, 1991

[54] METHOD FOR ANALYZING GASES ACCORDING TO THE COUNTER FLOW PRINCIPLE

[75] Inventor: Heinz D. Bürger, Wertheim, Fed. Rep. of Germany

[73] Assignee: Alcatel Hochvakuumtechnik GmbH, Wertheim, Fed. Rep. of Germany

[21] Appl. No.: 400,171

[22] Filed: Aug. 28, 1989

[30] Foreign Application Priority Data

Sep. 14, 1988 [DE] Fed. Rep. of Germany ....... 3831258

[51] Int. Cl.$^5$ .............................................. H01J 49/26
[52] U.S. Cl. .................................... 250/282; 250/289; 73/40.7
[58] Field of Search .................. 258/282, 289; 73/40.7

[56] References Cited

U.S. PATENT DOCUMENTS 4,195,224  3/1980  Sänger et al. ........................ 250/281
4,487,058  12/1984  Mennenga ................................ 73/40
4,550,593  11/1985  Reich .................................... 73/40.7
4,773,256  9/1988  Saulgeot ................................ 73/40.7

FOREIGN PATENT DOCUMENTS 864652  2/1971  Canada ................................ 250/289

Primary Examiner—Bruce C. Anderson
Attorney, Agent, or Firm—Sughrue, Mion, Zinn, Macpeak & Seas

[57] ABSTRACT

The invention resides in a method for analyzing gases according to the counterflow principle, comprising a mass spectrometer tube (3) located at the suction side of a molecular pump (2). The primary vacuum pressure is adjusted in such a way that basically ambiguous spectrometer indications can only result from a gas with low molecular weight reaching the mass spectrometer in counterflow to the molecular pump and not from a gas with higher molecular weight, which in itself would provoke a similar spectrometer indication.

5 Claims, 1 Drawing Sheet

METHOD FOR ANALYZING GASES ACCORDING TO THE COUNTER FLOW PRINCIPLE

BACKGROUND OF THE INVENTION

The invention relates to a method for analysing gases according to the counterflow principle, comprising a mass spectrometer tube located at the suction side of a molecular pump, both a primary vacuum pump and an inlet for the gases to be analysed being connected to the outlet of the molecular pump.

Because of the ionisation processes used, gas analysis methods employing mass spectrometers suffer from serious defects, which strongly reduce or even render impossible their applicability to several problems. These defects include the molecule fragmention during ionisation, which complicates the detection of the initially present molecules, because almost identical fragments can result from very different materials.

During ionisation, electrons are generally brought to a kinetical energy of at least 70 eV. At this energy level, the effective cross-sections and the ionisation efficiency present useful values, but the molecules are then fragmentated, which constitutes a decisive drawback. For example, the ionisation of carbon dioxide and carbon monoxide by electrons results in practically identical fragments and renders the separate detection of these two gases difficult.

Within certain limits, good results can be achieved by not only evaluating the main peak of the mass spectrometer, but the entire spectrum including the lateral peaks caused by the fragments, which signifies a so-called mass spectrometer fingerprint (see for example the periodical Vakuum 16, 67 (1966) "The interpretation of mass spectra in vacuum measurement"). However, many of the fingerprints are so similar, that their distinction becomes impossible. Thus, for example, the main peak of n-butane (mass 58) is located at mass 43 and the next following peak at mass 29, while acetone shows a main peak also at mass 43 and one of the secondary peaks at mass 29.

In order to avoid these difficulties in the interpretation of spectra, it has been proposed to proceed to a so-called soft ionisation, in order to reduce the creation of fragments as far as possible. Soft ionisation signifies a ionisation in two steps, the first step being constituted by the creation by electrons of a primary ion cloud of an inert gas. The primary ions are then mixed to the gas to be analyzed and, by means of charge transfer reactions, the different molecules of the gas to be analysed are converted into ions. The appropriate choice of primary ions having a ionisation potential, which is only slightly higher than that of the gas to be ionized, allows the neutral molecules to be transformed into ions without substantial fragmentation.

However, this method is too complicated for routine operations.

SUMMARY OF THE INVENTION

The object of the invention is therefore to propose a method which does not use soft ionisation and which nevertheless allows in many cases a clear distinction between fingerprints of similar structure.

According to the invention, this object is achieved by the fact that the compression ratio of the molecular pump is controlled in such a way that basically ambiguous spectrometre indications can only result from a gas with low molecular weight and no more from a gas with higher molecular weight, which in itself would provoke a similar spectrometer indication.

The invention is thus based on the fact that, in the frame of the counterflow gas analysis, light molecules reach with higher probability the analysis cell against the pumping direction of the molecular pump. In the case of turbomolecular pumps, a relatively sharp limit between relatively high and relatively low compression ratio is observed, while Holweck-type pumps ensure a higher control range at higher pressure.

The modification of the compression ratio of the molecular pump can be achieved according to a first embodiment of the inventive method by varying the primary vacuum total pressure.

In another embodiment of the inventive method, the compression ratio is modified by changing the speed of the molecular pump. If, however, a Holweck-type pump is used as molecular pump, it may be useful to modify the width of the annular gap or the length of the effective pumping area by elastic deformation of the stator wall or the relative axial displacement of the rotor with respect to the stator.

BRIEF DESCRIPTION OF THE DRAWINGS

On the basis of the attached drawings, the invention will now be explained in more detail.

DETAILED DESCRIPTION

Figure 1:
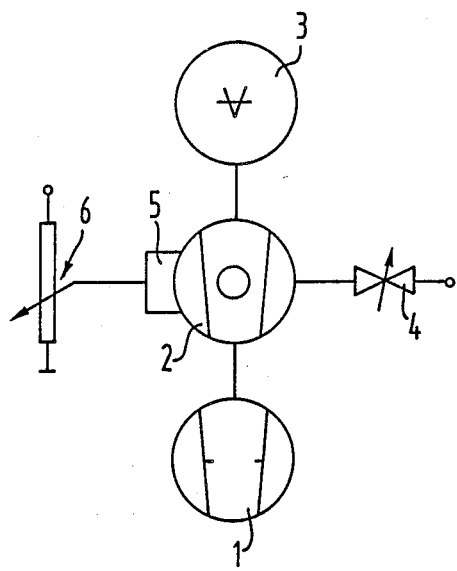
FIG. 1 shows a device in which the method according to the invention can be implemented.

The spectrometer device according to FIG. 1 consists of a pumping set comprising a primary vacuum pump 1 and a Holweck-type molecular pump 2 as well as a mass spectrometer cell 3 located at the suction side of the molecular pump 2. At the discharge side of this pump or at an intermediate inlet thereto, the gas to be analysed is supplied via an inlet valve 4. The molecular pump 2 is driven by a motor provided with a regulator 6 for setting the rotational speed. It is known that the compression ratio of the molecular pump 2 depends on the rotational speed of this pump. At increasing speed, preferably light molecules are transferred to the mass spectrometer cell in counterflow to the pumping direction. Thus, the rotational speed can be defined in such a way that at a given ratio between partial pressure and primary vacuum pressure, propane can still reach the mass spectrometer cell, but no carbon dioxide or formic acid or butane or acetone or acetic acid or pump oil etc., which all present similar fingerprints with a peak at mass 43 and another peak at mass 44.

Figure 2:
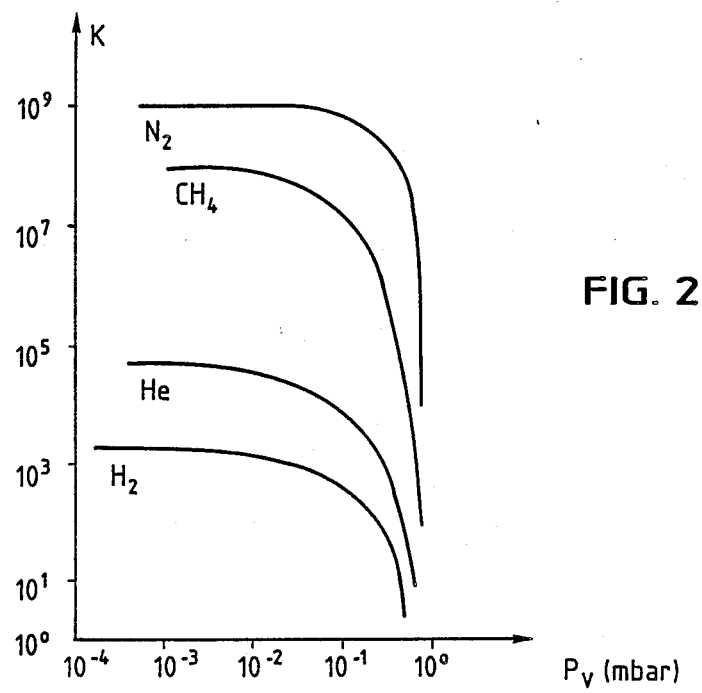
FIG. 2 shows the interdependence between the compression ratio of a turbomolecular pump and the primary vacuum pressure for different gases.

Another possibility to selectively modify the compression ratio of the molecular pump consists in the modification of the primary vacuum pressure. FIG. 2 shows a typical diagram for the dependence of the compression ratio K from the primary vacuum pressure $p_v$ (in millibar) for a turbomolecular pump. It can be seen, that at high primary vacuum pressure (coarse primary vacuum), molecules of a greater mass can diffuse through the turbomolecular pump to the mass spectrometer cell than at a better primary vacuum.

Other possibilities to control the selectivity of retrodiffusion consist in increasing or decreasing the radial gap between the smooth wall and the wall containing the Holweck grooves of the pump, in such a way that, the spiral grooves being cut into the rotor, the cylindrical stator wall constitutes a diaphragm made of resilient steel, the diameter of which can be hydraulically modified. This technique is for example known from the so-called hydroexpansion sleeves.

On the other hand, the compression ratio of the molecular pump can also be achieved by displacing axially the stator with respect to the rotor. By this means, the pumping area is shortened or lengthened and the compression ratio is modified.

I claim:

1. In a method for analysing gases according to the counterflow principle by sensing counterflow of gas to be analysed to a mass spectrometer via a mass spectrometer tube located at the suction side of a molecular pump coupled to a primary vacuum pump and an inlet for the gases to be analyzed connected to the outlet of the molecular pump, the improvement comprising the step of controlling the compression ratio of the molecular pump in order to prevent gases of a higher molecular weight from passing through the molecular pump in the counterflow direction to the mass spectrometer and measuring the fingerprint of the gas at said spectrometer, whereby a change in fingerprint signifies that a gas of higher molecular weight under consideration is present in the unknown gas being analyzed.

2. A method according to claim 1, wherein the compression ratio of the molecular pump is controlled by modifying the primary total pressure of the primary vacuum pump by changing the rotational speed of the primary vacuum pump.

3. A method according to claim 1, wherein said molecular pump is a Holweck-type pump and the compression ratio of the molecular pump is controlled by changing the width of an annular gap between a rotor and a stator of said Holweck-type pump.

4. A method according to claim 1, wherein said molecular pump is a Holweck-type pump and the compression ratio of the molecular pump is controlled by changing the length of the pumping area by displacing axially and relatively a rotor with respect to a stator of said Holweck-type pump.

5. A method according to claim 1, wherein the compressor ratio of the molecular pump is controlled by modifying the primary total pressure of the primary vacuum pump by varying the inlet opening of a variable gas inlet at the connection between the primary pump and the molecular pump.

* * * * *